United States Patent [19]

Bellows

[11] Patent Number: 5,073,499
[45] Date of Patent: Dec. 17, 1991

[54] CHEMICAL DIAGNOSTIC SYSTEM

[75] Inventor: James C. Bellows, Maitland, Fla.

[73] Assignee: Westinghouse Electric Corp., Pittsburgh, Pa.

[21] Appl. No.: 182,019

[22] Filed: Apr. 15, 1988

[51] Int. Cl.$^5$ .................. G01N 1/16; G01N 31/04; G01N 31/08; G06F 15/46

[52] U.S. Cl. .................................. 436/50; 422/62; 422/81; 422/82; 422/105; 364/496; 364/497; 436/55

[58] Field of Search .............. 436/50, 55; 422/105, 422/81, 82.02, 82, 82.01, 62; 364/496, 497, 498, 499, 500, 501, 502, 503, 504, 506, 551.01, 551.02, 172; 134/10, 56 D, 108, 113

[56] References Cited

U.S. PATENT DOCUMENTS

| | | | |
|---|---|---|---|
| 4,172,014 | 10/1979 | Sequeira et al. | 364/501 |
| 4,181,951 | 1/1980 | Bolke | 364/499 |
| 4,206,504 | 6/1980 | Frey | 364/497 |
| 4,298,955 | 11/1981 | Munday et al. | 364/500 |
| 4,396,435 | 8/1983 | West et al. | 134/10 |
| 4,402,910 | 9/1984 | Smith et al. | 422/62 |
| 4,414,858 | 11/1983 | Peterson et al. | 73/863.33 |
| 4,472,354 | 9/1983 | Passell et al. | 422/83 |
| 4,587,518 | 5/1986 | King | 210/85 |
| 4,713,772 | 12/1987 | Carlson | 364/496 |
| 4,722,830 | 2/1988 | Urie et al. | 422/81 |
| 4,766,550 | 8/1988 | Byers et al. | 364/497 |
| 4,822,744 | 4/1989 | Bellows | 422/82.02 |
| 4,830,757 | 5/1989 | Lynch et al. | 364/500 |
| 4,855,061 | 8/1989 | Martin | 364/500 |

OTHER PUBLICATIONS

A. J. Gonzalez, R. L. Osborne, C. T. Kemper, On-Line Diagnosis of Turbine-Generators Using Artificial Intelligence, IEEE Transactions on Energy Conversion, vol. EC-1, No. 2, Jun. 1986.

R A E Sargeant, Expert Systems for Process Control Rooms, Measurement + Control, vol. 19, Nov. 1986, pp. 239-244.

W. Leidig and H. Seiler, Criteria Computer for Diagnostics in Power Plants, Siemens Power Engineering & Automation VIII, (1986) No. 1, pp. 28-32.

EPC Search Report conducted May 29, 1990 at Berlin by Examiner Johnson K. M.

Harvey M. Wagner, Principles of Operations Research With Applications to Managerial Decisions.

Primary Examiner—David L. Lacey
Assistant Examiner—Kimberly A. Trautman

[57] ABSTRACT

A chemical monitor system is disclosed that controls a multiplexable valve array 90 to route a fluid sample from any of plural fluid sample sources 20-38 to any of plural monitors 142-160 which will produce the most valuable chemistry measurement for diagnosing any existing or suspected malfunction. Fluid regulators 170-188 keep the flow rate constant regardless of the number of monitors 142-160 connected to a particular source. A computer 200 configures the array 90 based on the usefulness of sample analysis to a disgnostic system.

12 Claims, 5 Drawing Sheets

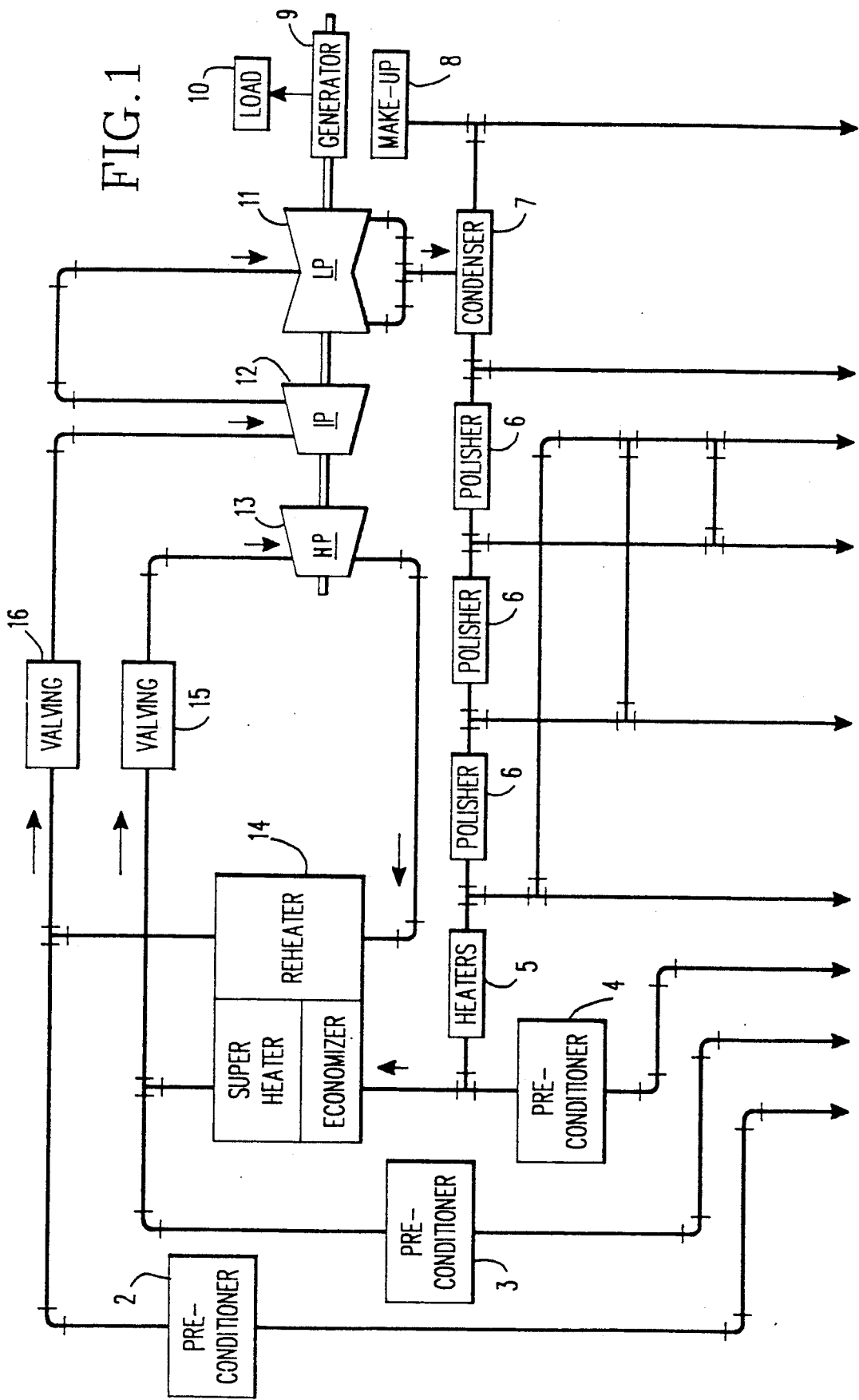

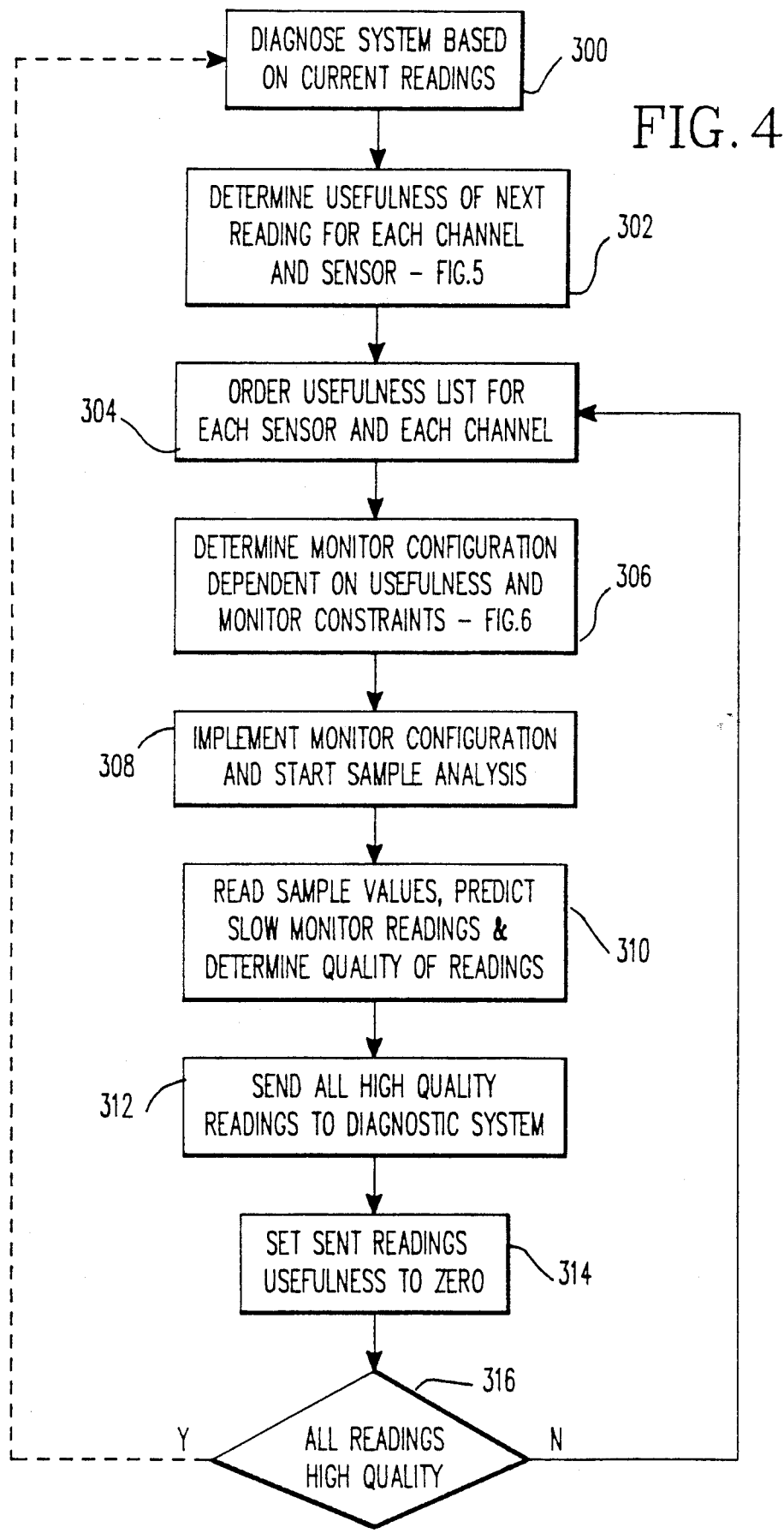

CHEMICAL DIAGNOSTIC SYSTEM

BACKGROUND OF THE INVENTION

1. Field of the Invention

The present invention is directed to a chemistry monitor system for a power plant that selects the most valuable next sample and, more particularly, to a system that uses the usefulness of the samples to control which chemistry monitors analyze the next sample and the source of the sample.

2. Description of the Related Art

Correct water and steam chemistry is critical to the prevention of corrosion in steam driven power plants. A number of locations around the steam cycle must be sampled and analyzed to know that the chemistry is correct and to understand why chemistry imbalances occur. Current practice varies from a minimum of a daily collection of samples from a few locations and manual analysis of a few chemical properties of the samples to a maximum of dedicated on line monitors for every possible chemical being analyzed and at every location or source from which samples are taken. The dedicated monitors are frequently supplemented by manual analysis of chemical species for which on-line monitors are not available. The daily collection of samples does not allow a sufficiently rapid adjustment of plant chemistry to prevent corrosion problems from occurring. The use of the maximum number of dedicated monitors is very expensive in all but the very largest and most efficient power plants. When a chemical imbalance occurs, manual analysis in all cases is increased in frequency and in the variety of chemical species for which amounts are determined In addition, during an imbalance, samples from special sample locations may be collected to specifically analyze the problem so that corrective action may be taken. U.S. Pat. No. 4,414,858 describes a valving system where samples from multiple streams are directed to an analyzer on a periodic fixed schedule basis by a computer.

SUMMARY OF THE INVENTION

It is an object of the present invention to reduce the costs of chemistry monitoring systems as compared to those systems which provide a monitor for each stream and species being sampled.

It is also an object of the present invention to increase sampling speed and frequency over the manual sampling method.

It is another object of the present invention to provide a chemistry monitoring system which adapts to the changes in the chemistry of the system being monitored.

It is an additional object of the present invention to maximize sampling efficiency so that continuous sampling is possible and economically efficient, allowing fine tuning of the plant chemistry thereby increasing plant life expectancy.

The above objects can be attained by a system that controls multiplexable valves to route a fluid sample from any fluid sample source to a particular monitor among a plurality of monitors which will produce the most valuable chemistry measurement for diagnosing any existing or suspected malfunction.

These together with other objects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 depicts typical sample sources for a steam turbine power generation system;

FIG. 4 is a flowchart of the operations performed by the present invention;

DESCRIPTION OF THE PREFERRED EMBODIMENTS

The present invention uses artificial intelligence diagnostic techniques to determine which fluid line should be sampled next and which type of sample measurement should be made. An artificial intelligence diagnostic system works by developing confidence in the presence or absence of a specific equipment malfunction or condition based on sensor input data. A malfunction is defined as a condition where something is not functioning as needed for whatever reason, for example, a sodium imbalance. The artificial intelligence system examines the effect of a change in a chemical monitor input and how it changes the confidence in the specific diagnoses that are under consideration. The variable with the largest potential to change the diagnosis, either to confirm or disconfirm or to separate two competing diagnoses, is the most valuable variable, source fluid and analysis type to be measured next. If this variable has just been measured, its value is known and an additional measurement of the value is itself of little value. Thus, the time since the last measurement is an important criteria in determining the value of remeasuring a particular variable.

Figure 2A:
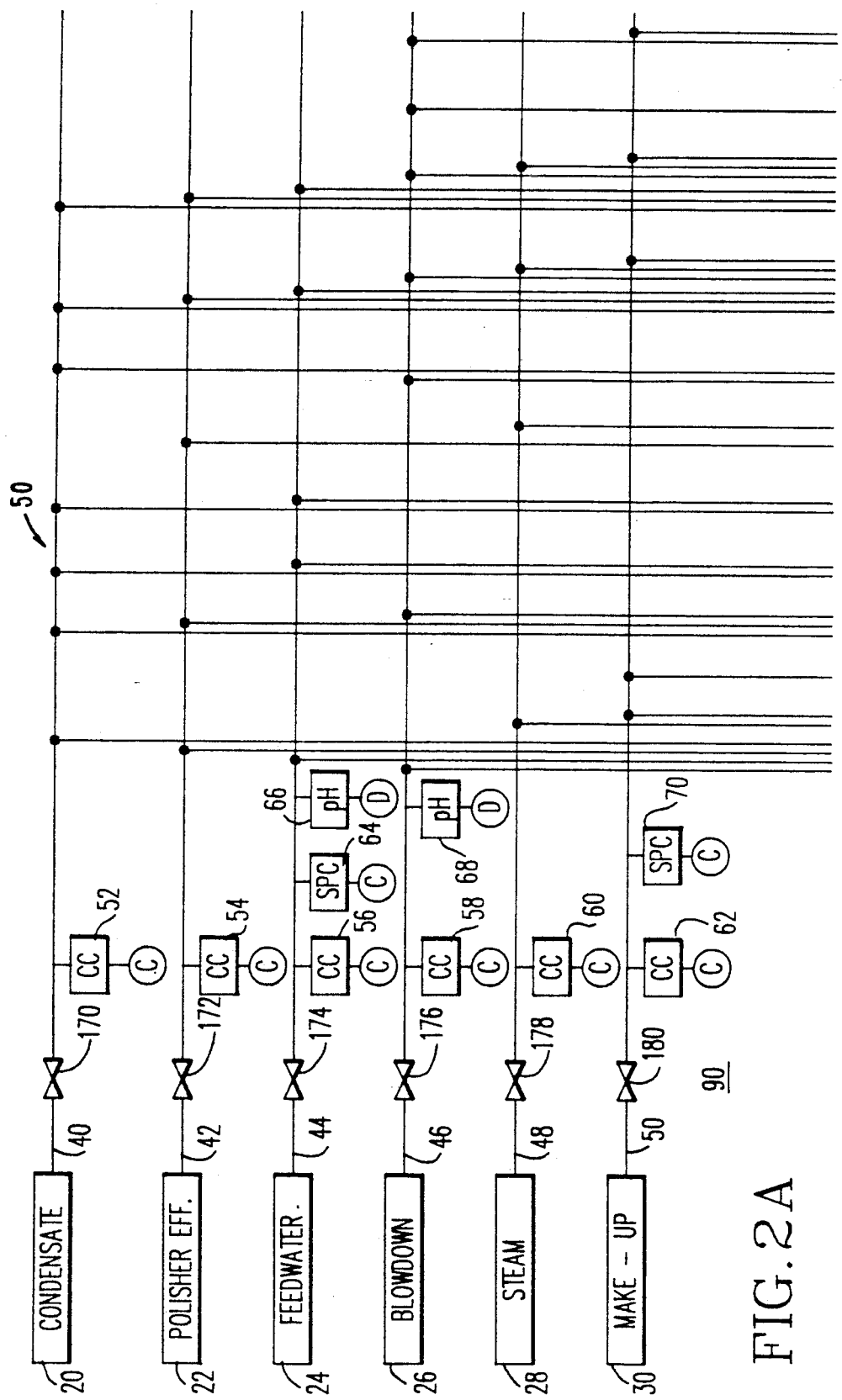
FIG. 2A and FIG. 2B, illustrates the monitor, valve and pipe configuration of the present invention for a representative plant.
Figure 2B:
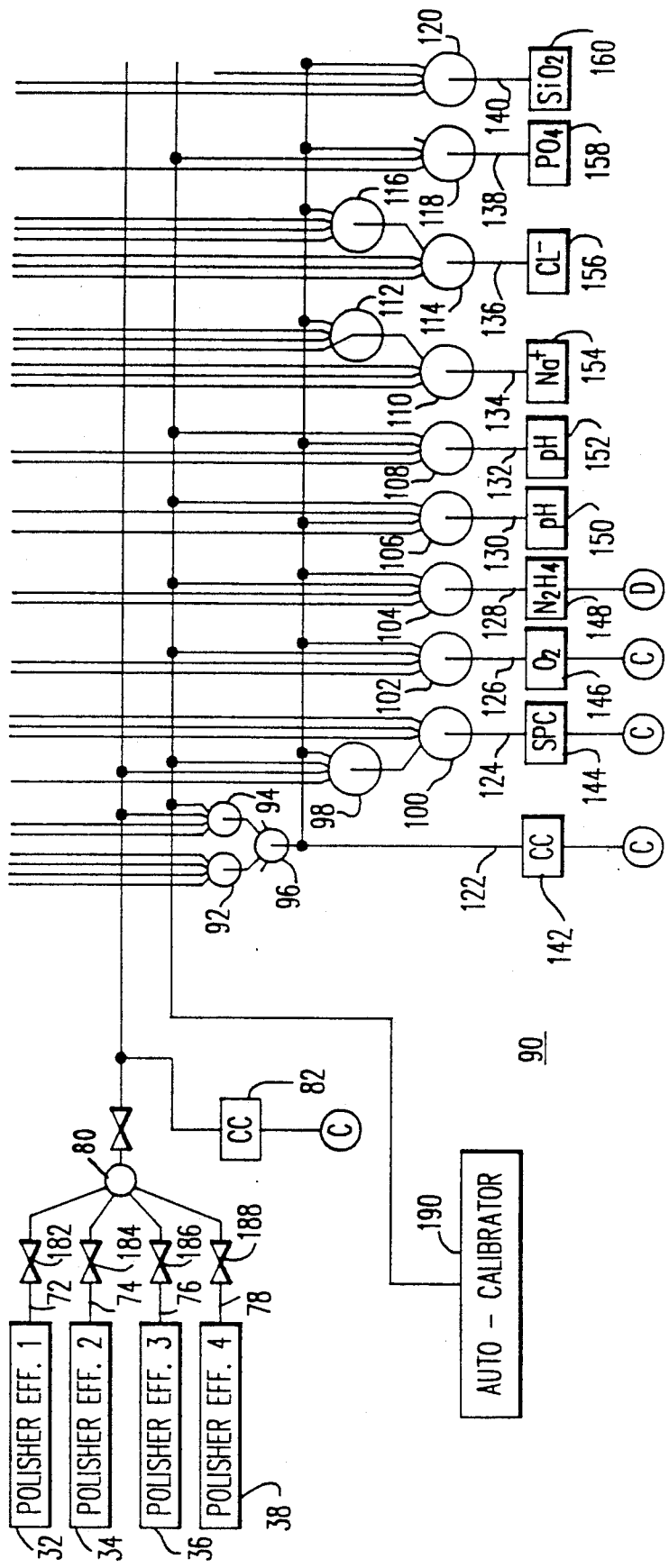

The present invention analyzes fluid samples from several different locations (sources) in a steam generator power plant including the make up system 8 which provides water to the system as illustrated in FIG. 1. This figure illustrates a typical steam turbine system for a power plant and includes a steam turbine arrangement having a plurality of turbines in the form of a high pressure turbine 13, an intermediate pressure turbine 12 and a lower pressure turbine 11, all of which are coupled to a common shaft to drive an electrical generator 9 which supplies power to a load 10. A steam supply in the form of a boiler system 14 includes, by way of example, an input economizer section, a super heater section and a reheater section. Boiler steam is provided to the turbine arrangement through input valving 15 and steam exiting the higher pressure turbine is reheated in the reheater section and provided to intermediate pressure turbine 12 through valving 16. Steam exiting the intermediate pressure turbine 12 is provided by way of crossover piping to the low pressure turbine 11 from which the steam is exhausted into a conventional condenser 7. Water in the condenser is recirculated back to the boiler after chemical treatment to maintain high purity. The chemical treatment may include a plurality of polishers 6 which basically are ion exchange units designed to remove impurities. After the chemical treatment the water is heated by a series of heaters 5 and returned to the input economizer of the boiler system 14. A sampling system 50 is provided in accordance with the present invention to automatically obtain samples from various points in the steam turbine system. Since some of the fluid samples might be at elevated temperatures and pressures, a plurality of preconditioners 2-4 are provided to reduce temperatures and pressures of the circulating fluid to manageable values. This typical steam turbine system is described in more detail in U.S. Pat. No. 4,414,858 previously mentioned. The sampling system contains a combination of dedicated and multiplexed monitors as illustrated in FIGS. 2A and 2B. Each source line 40, 42, 44, 46 and 48 includes a dedicated cation conductivity monitor 52, 54, 56, 58, 60 and 62. Selected source lines 44, 46 and 50 include other types of monitors 64, 66, 68 and 70 such as PH and SPC (specific conductivity). Individual polisher effluent source lines 72, 74, 76 and 78 are multiplexed through a conventional 4-to-1-multiplexing valve 80 to a single cation monitor 82. After the source fluid passes the dedicated monitors 52, 54, 56, 58, 60 and 62 it enters a piping multiplex array 90 which includes several 4-to-1 multiplexing valves 92, 94, 96, 98, 100, 102, 104, 106, 108, 110, 112, 114, 116, 118 and 120 which will supply source fluid from any source line 42, 44, 46, 48, 50, 72, 74, 76 and 78 to any sample line 122, 124, 126, 128, 130, 132, 134, 136, 138 and 140, so that fluid from any source line can be analyzed by any of the chemical monitors 142, 144, 146, 148, 150, 152, 154, 156, 158 and 160. Similar schemes can be produced using on-off or other multiplex valves such as a 3-to-1 valve. By providing such a multiplex pipe array 90, if a sodium sample from the condensate effluent source 20 is the most valuable sodium sample and the most valuable oxygen sample is from the feedwater source 24, the system can connect these two sample lines to the appropriate sensors at the same time. It is also possible to connect the condensate source 20 to several of the monitors 144, 146, 148, 150, 152, 154, 156, 158 and 160 at the same time.

Disturbing the rate of flow through a sample line can alter the sample composition temporarily. For this reason, the monitor system contains flow and pressure regulators 170, 172, 174, 176, 178 and 180 in FIG. 2A and 182, 184, 186 and 188 in FIG. 2B which keep the total sample line flow pressure, from for example polisher effluent sources 32, 34, 36 and 38 of the polishers 6, constant as more or fewer of the monitors are connected to the specific source line and keep the flow rate through the monitors constant. The pressure provided to the monitors should consistently be approximately 20 pounds square inch and the regulators 170, 172, 174, 176, 178, 180, 182, 184, 186 and 188 allow the pressure to be properly maintained. The maximum flow rate through any regulator can be calculated by determining the maximum number of monitors which will be connected to the source line by summing the constant flow rates through the monitors. A low sample flow is preferred because the water being sampled in a steam generator power plant is extremely high purity water which is expensive to make. A low sample flow rate is thus an economic advantage to the user.

There is a time lag from the time a multiplexed monitor has been attached to a sample line until the time it is providing an accurate reading. This time lag consists of two parts, the first is the dead volume of the lines and the monitor which can be reduced by shortening the lines and the second is the response time of the monitor. Conductivity monitors are comparatively fast in making their measurement, while selective ion electrode monitors can be slow with time constants on the order of several minutes. The present invention by allowing the source lines to be multiplexed to a particular sample line and with the provision of flow regulators, allows a faster monitor to analyze several samples from different source lines while a slower monitor is analyzing a single sample possibly from the same source line from which the faster monitor makes a quicker analysis. To minimize the second lag time caused by the selective ion monitors, the data from the monitor can be analyzed and a stable value predicted using conventional extrapolation techniques. In this data analysis, the time constant and quality of fit to a predicted function is determined to provide a point in time at which a prediction can be made from an on-going analysis. If the quality of fit is good, the predicted value can be used in place of a later obtained stable reading and the wait for a stable reading can be eliminated allowing the monitor to be moved to the next source increasing the number of data points available from the monitor per unit of time.

In the event that the quality of fit for predicting the stable value of an analysis is not good and a predetermined time limit has been reached at which a best diagnosis for the data is necessary, the data analysis can fit the data to an equation which represents the approach of a monitor to a linearly changing concentration as set forth below:

$$x = a + bt + ce^{-kt} \quad (1)$$

where the coefficients can be identified with the initial value of the sensor $x_0$, the true value of the sensor at $t=0$, $x_t$, the rate of change of the true concentration r and the time constant of the sensor k as set forth below:

$$a = x_0 - r/k \quad (2)$$

$$b = r \quad (3)$$

$$c = x_0 - x_t + r/k \quad (4)$$

The use of such extrapolation and linear fitting allows the analysis time to be reduced to a minimum.

Additionally, by monitoring the time constant of a selective ion monitor the condition of the monitor can be determined. If the time constant increases excessively, manual attention is required for the monitor. By providing an autocalibrator 190 connectable through the multiplex array 90 to the monitors 142, 144, 146, 148, 150, 152, 154, 156, 158 and 160, the time constant for each monitor can be periodically determined. An appropriate autocalibration system can be found in U.S. Pat. No. 4,713,772. The autocalibration system ensures that substantial step changes in fluid concentration will be supplied to each monitor on a regular basis to provide good determinations of the time constant of the monitor. By providing several sensors of the same type, the array 90 also allows the consistency between sensors to be evaluated by successive or simultaneous analysis of the same fluid by two or more identical sensors.

Figure 3:
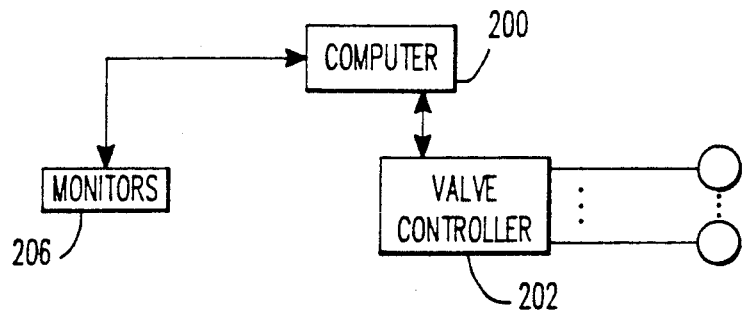
FIG. 3 illustrates the control hardware of the present invention.

The valves are controlled by a computer 200 through a conventional digital valve controller 202 or those supplied by the valve manufacturer as illustrated in FIG. 3 to supply the fluid to monitors 206 (144, 146, 148, 150, 152, 154, 156, 158 and 160). The computer 200 ispreferably a Digital Equipment VAX 8500 series computer and executes an expert system program that uses knowledge representations and inference procedures to reach conclusions. Many expert systems are available which will accomplish the goals of the present invention, however, the preferred system is PDS (Process Diagnosis System) described in the proceedings of the Eighth International Joint Conference on Artificial Intelligence, Aug. 8-12, 1983, pp. 158-163 incorporated by reference herein. The PDS system is available from Westinghouse and a detailed description of the system can be found in U.S. Pat. No. 4,649,515, incorporated by reference herein. An example of the use of this system to diagnosis malfunctions can be found in U.S. Pat. No. 4,644,479 incorporated by reference herein. Packages specifically for diagnosing chemical malfunctions such as CHEMAID are available from Westinghouse for fossil power plants.

In the PDS system, as well as other expert systems, for each rule there is evidence as well as a consequence (hypothesis) of that evidence. In PDS evidence is linked to a hypothesis by a rule with the evidence and hypothesis constituting nodes of the system. Associated with each node (hypothesis) is a measure of belief as well as a measure of disbelief which both range on a scale from 0 to 1. The difference between the measure of belief and the measure of disbelief yields a confidence factor (CF) which ranges from $-1$ to $+1$ where more positive numbers indicate that the hypothesis is likely true. An expert in the chemistry associated with the plant equipment being monitored establishes the various rules and relationships which are stored in the computer memory.

Figure 5:
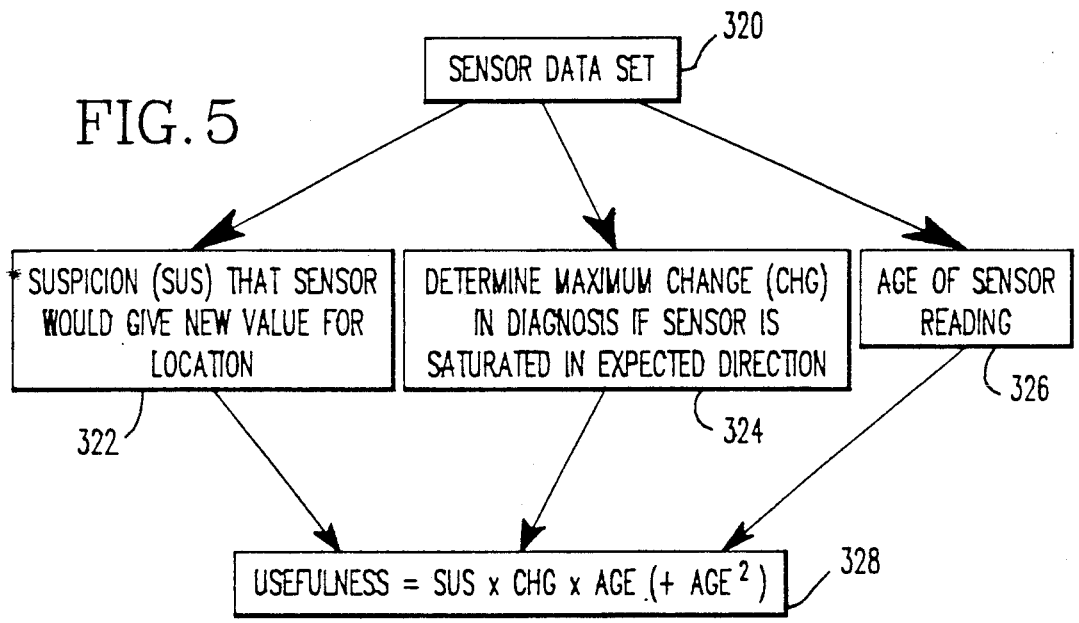
FIG. 5 illustrates how the usefulness of a monitor reading is determined.
Figure 6:
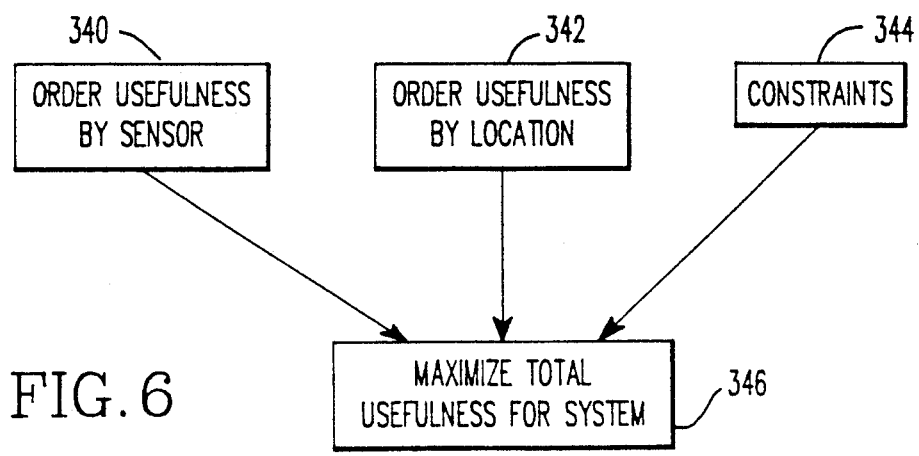
FIG. 6 illustrates determination of a new sampling configuration.

The expert's belief in the sufficiency of a rule can also be considered by PDS and represents the experts opinion on how the evidence supports the hypothesis and is designated as a sufficiency factor where positive values of the sufficiency factor denote that the presence of evidence suggests that the hypothesis is true. The PDS expert system can also utilize the experts belief in the necessity of the rule which indicates to what degree the presence of the evidence is necessary for the hypothesis to be true. The necessity belief is designated as a necessity factor. The expert system using a package such as the CHEMAID package mentioned above running in parallel with the expert system of the present invention diagnoses chemical malfunctions 300 based on the current readings as illustrated in FIG. 4. The diagnostic system preferably has a required diagnosis cycle of for example 10 minutes. This diagnosis also provides confidence factors which indicate the likelihood that the monitor reading from a particular source will change in the near future. These confidence factors along with other data, as will be discussed with respect to FIG. 5, are used to determine 302 the usefulness of the next fluid reading for each monitor and monitor. Once the usefulness for each channel, where a channel is a combination of a source and a sensor, is determined the sensors and sources are sorted 304 in a descending order of usefulness. From this usefulness list, the system determines 306 the monitor configuration which will maximize the total usefulness of the system. Next, the monitor configuration with the maximum usefulness is implemented 308 and sample analysis is started. As previously discussed the monitors can have different convergence rates to a quality reading. The sample values produced by the monitors are read 310 and for slow monitor readings the final value of the reading is determined along with its quality using standard prediction and statistical analysis techniques as previously discussed.

The readings with a quality above a predefined threshold, such as when three successive determinations of the final value are equal at the 95% confidence level, are sent 312 to the diagnostic system using a conventional technique such as loading the sensor readings into a common memory used by both the diagnosis system and the monitor control system discussed herein. The diagnostic system can then use the most recent sensor value to provide an updated diagnosis even while the slower sensors are settling toward a high quality reading. After the readings are sent, those readings that have been sent have their usefulness set 314 to zero. If all the readings have a quality 314 above the predetermined threshold, the diagnosis system is informed by for example setting a flag in the common memory. Once this flag is set the diagnostic system, after it performs the next diagnosis, informs the monitor control system that another monitor configuration and sampling cycle is appropriate. If all the readings are not of high quality 316, the usefulness list is reordered 304 to produce another monitor configuration. The cyclic reconfiguration continues to occur until the usefulness list is exhausted or until the diagnostic system updates the information upon which the usefulness list is based.

The usefulness of the next reading for each source and sensor can be determined using a brute force method such as executing the CHEMAID diagnostic system with the maximum and minimum possible sensor values and with expected change values and determining which sensor value would most drastically change or provide the greatest expected change in the current diagnosis. Such a brute force method will be very time consuming. An alternative is illustrated in FIG. 5. The sensor data set 320 includes the confidence factors for the latest monitor readings, the time since the last reading, and high and low saturation values for the monitors. From this data set 320, the suspicion that a monitor would give a new value for a particular source is determined 322. This determination is made in accordance with $SUS = 1 - CF$ (no change) where the confidence factor CF is determined by the conventional CHEMAID type diagnostic system using a rule such as set forth below.

| | |
|---|---|
| CONTEXT: | always |
| EVIDENCE: | (I and steady-Na-C steady-catcond-C steady-speccond-C) |
| HYPOTHESIS: | no-change-Na-C |
| SF: | 0.6 |
| NF: | 0.6 |
| DESCRIPTION: | If the condensate sodium was steady as of last reading and the cation and specific conductivities on the condensate have been steady, then there is substantial belief that the condensate sodium has not changed. |

As an alternative this suspicion can be determined by conventional forward chaining in the diagnostic system.

Along with the suspicion of change the direction of the change can be determined by comparing the current monitor reading with the most recent previous monitor reading. Once the expected direction of monitor change is determined from the sensor data set 320 the maximum change in the diagnosis, if the sensor is saturated in the expected direction, is determined 324 using the conventional diagnostic system such as CHEMAID. This can be done by holding all other chemical malfunction data constant and changing the reading of interest to the maximum saturation value. The change could also be the sum of all diagnostic changes based on saturated sensors. Alternately, the value could be the change value calculated for the highest priority malfunction, if the diagnostic system ranks the malfunctions in accordance with priority as set forth in pending U.S. application filed February 1988, entitled "Automated System To Prioritize Repair Of Plant Equipment" by J. C. Bellows, R. L. Osborne and A. Gonalez and having U.S. Ser. No. 07/156,064. In most cases the change due to a single variable is the most appropriate. A person of reasonable skill in diagnosing power plant problems would recognize special situations where pairs or larger combinations of monitors would be specifically more useful than a single variable, for example, looking for hydroxide versus salt one wants simultaneous $Na^+$, $Cl^-$, pH and cation conductivity measurements.

The third consideration used to determine usefulness is the age 326 of the monitor reading which is determined by comparing the current time with the time at which the most recent monitor reading was taken. The usefulness is the product 328 of the suspicion (SUS), the maximum change (CHG) and the age (AGE) of the reading. To be certain that a particular sample point is not continually missed because there is no suspicion of a change and no expected change in the diagnosis, the square of the sample age could be added (as indicated by the parenthesis in block 328) to the product. Adding the square of the age will eventually produce a usefulness value which would rise to the top of the usefulness list.

The determination of the monitoring configuration during each sample cycle is performed using the order of usefulness by sensor 340, the order of usefulness by location (source) 342 and the constraints 344 on the monitors. One constraint would be total flow from a source line (where different monitors have different required flows) to a particular source, another constraint would be that the monitor is currently occupied doing a reading, and still another constraint might be the need for simultaneous readings of two or more variables. One way the monitor configuration can be determined by maximizing 346 the total usefulness for the system is to sort all type samples and locations by usefulness. This list is then examined from top to bottom selecting monitors for particular source channels and flagging those selected monitors as in use. The usefulness list would be scanned from top to bottom or until all monitors are occupied. For example if the partial list of usefulness values contained:

| Source | Sample Type | Usefulness |
| --- | --- | --- |
| Condensate | $Na^+$ | 98 |
| Condensate | $Cl^-$ | 97 |
| Make-up | $Na^+$ | 96 |
| Feedwater | $O_2$ | 96 |
| Blowdown | pH | 30 |
| Steam | pH | 22 |
| Polisher Effluent | $Cl^-$ | 10 |

With such a list the condensate source 20 would be connected to monitors 154 ($Na^+$) and 156($Cl^-$), the make-up source 30 would not be connected since the sodium monitor 154 is busy, the feedwater source would be connected monitor 146, the blowdown source 26 would be connected to monitor 152 and the polisher effluent source 22 would be unconnected. After the monitor 154 finished its sample the array 90 would be reconfigured to connect monitor 154 to the make-up source 30. When monitor 156 finished it would be connected to polisher effluent source 22. Another scheme which can be used to generate a maximum usefulness configuration is a conventional hill climbing scheme.

Whichever type of configuration determination algorithm is used it is not necessary to be certain that the most useful configuration is selected. A nearly most useful configuration produces a set of data which reduces the usefulness of all similar configurations and will tend to make the missed reading appear in the next configuration. As a result being trapped on a relative maximum is not a disaster, because taking those readings places those reading values at a relative minimum at that configuration for the next configuration cycle.

The present invention benefits the user by providing a minimum of costly chemical sampling instruments at a minimum loss in actual chemical sampling information. In addition, because of the inclusion of the autocalibration system, the condition of the monitors is continuously monitored thereby reducing the need for manual attention to the monitor system to those times when attention is actually needed.

The many features and advantages of the invention are apparent from the detailed specification and, thus, it is intended by the appended claims to cover all such features and advantages of the invention which fall within the true spirit and scope thereof. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

I claim:

1. A method of monitoring fluid from fluid sources using a piping array to route fluid from any source to any of plural chemical monitors in a processing system being monitored for chemical malfunctions by a diagnostic system, comprising the steps of:
   (a) diagnosing a malfunction of the processing system using the diagnostic system;
   (b) determining a usefulness of an analysis of each source fluid by each monitor where usefulness comprises a greatest expected change in a malfunction diagnosis confidence when each monitor is saturated in an expected direction;
   (c) determining and implementing a configuration of the piping array from the usefulness; and
   (d) sampling the fluids, analyzing the fluids and providing the results to the diagnostic system.

2. A method of monitoring fluid from fluid sources using a piping array to route fluid from any source to any of plural chemical monitors in a processing system being monitored for chemical malfunctions by a diagnostic system, comprising the steps of:
   (a) diagnosing a malfunction of the processing system using the diagnostic system from
   (b) determining a usefulness of an analysis of each source fluid by each monitor;

USEFULNESS=SUS*CHG*AGE

, where SUS is the suspicion that a monitor will produce a new value for the analysis of the source fluid, CHG is the maximum change in the malfunction diagnosis if the monitor is saturated in an expected direction and AGE is an age of a most recent monitor analysis (c) determining and implementing a configuration of the piping array from the usefulness; and (d) sampling the fluids, analyzing the fluids and providing the results to the diagnostic system.

3. A method as recited in claim 2, wherein usefulness is further defined by adding $AGE^2$.

4. A method as recited in claim 1, wherein step (c) includes performing a hill climbing algorithm to maximize the total usefulness of a combination of analyses.

5. A method as recited in claim 1, wherein step (c) includes the steps of:
   (ci) ordering usefulness from highest to lowest;
   (cii) determining a configuration from the ordered usefulness; and
   (ciii) implementing the configuration; and wherein step (d) includes the steps of:
   (di) providing analysis values above a predetermined quality to the diagnostic system and continuing analysis for analysis values below the predetermined quality; and
   (dl) setting the usefulness of each analysis provided to the diagnostic system to zero.

6. A method of monitoring fluid from fluid sources using a piping array to route fluid from any source to any of plural chemical monitors in a power plant being monitored for chemical malfunctions by a diagnostic system, comprising the steps of:
   (a) diagnosing a malfunction of the power plant using the diagnostic system;
   (b) determining a usefulness of an analysis of each source fluid by each monitor from:

$$USEFULNESS = SUS*CHG*AGE + AGE^2$$

, where SUS is the suspicion that a monitor will produce a new value for the analysis of the source fluid, CHG is the maximum change in the malfunction diagnosis if the monitor is saturated in an expected direction and AGE is an age of a most recent monitor analysis;
   (c) determining and implementing a configuration of the piping array from the usefulness, including the steps of:
   (ci) ordering usefulness from highest to lowest;
   (cii) determining a configuration from the ordered usefulness; and
   (ciii) implementing the configuration; and
   (d) sampling the fluids, analyzing the fluids and providing the results to the diagnostic system including steps of:
   (di) providing analysis values above a predetermined quality to the diagnostic system and continuing analysis for analysis values below the predetermined quality; and
   (dl) setting the usefulness of each analysis provided to the diagnostic system to zero.

7. A chemical diagnostic system for monitoring fluid sources, said diagnostic system comprises:
   at least two different chemical monitors for analyzing fluids from the fluid sources;
   piping means for transmitting the fluids from the fluid sources to any of and each of said chemical monitors simultaneously; and
   control means coupled to said piping means for determining which fluid from the fluid sources to supply to at least one of said chemical monitors in dependence on the fluid which has a highest usefulness where usefulness comprises a greatest expected change in a malfunction diagnosis when each of said chemical monitors is saturated in an expected direction.

8. A system as recited in claim 7, further comprising pressure regulators positioned in said piping means so as to maintain a constant flow through said piping means to said at least two different chemical monitors.

9. A system as recited in claim 7, further comprising dedicated chemical monitors positioned so as to monitor each of the fluid sources.

10. A system as recited in claim 7, wherein said piping means comprises multiplexable fluid valves positioned and arranged so as to deliver the fluid flow from the fluid sources to said at least two different chemical monitors.

11. A chemical diagnostic system for monitoring fluid sources, said diagnostic system comprises:
    at least one flow regulator connectable to each of the fluid sources for regulating fluid flow;
    at least one dedicated chemical monitor connected to said at least one flow regulator;
    at least two different chemical monitors for analyzing fluids from the fluid sources;
    multiplexable fluid valves connected between said at least one flow regulator and said at least two different chemical monitors, and transmitting fluid from said at least one flow regulator to any of and each of said at least two chemical monitors simultaneously; and
    control means coupled to said multiplexable fluid valves for determining which fluid from the fluid sources to supply to at least one of said dedicated chemical monitor and said at least two different chemical monitors in dependence on the fluid which has a highest usefulness where usefulness comprises a greatest expected change in a malfunction diagnosis when said at least one of said dedicated chemical monitor and said at least two different chemical monitors is saturated in an expected direction.

12. A chemical diagnostic system for monitoring fluid sources, said diagnostic system comprises:
    different chemical monitors each for analyzing fluids from the fluid sources;
    a pipe and valving system positioned and arranged so as to deliver the fluid flow from the fluid sources to said different chemical monitors and to transmit the fluids from any of the fluid sources to any of and each of said different chemical monitors; and
    reconfiguration means coupled to said pipe and valving system for routing the fluid to different ones of said different chemical monitors in dependence on the fluid which has a highest usefulness where usefulness comprises a greatest expected change in a malfunction confidence when each said different chemical monitor is saturated in an expected direction.

* * * * *